US009910021B2

(12) United States Patent
Chang et al.

(10) Patent No.: US 9,910,021 B2
(45) Date of Patent: Mar. 6, 2018

(54) LOW POWER SENSOR FOR NON-REACTIVE GASES

(71) Applicant: International Business Machines Corporation, Armonk, NY (US)

(72) Inventors: Josephine B. Chang, Bedford Hills, NY (US); Jiaxing Liu, New York, NY (US); Theodore G. van Kessel, Millbrook, NY (US)

(73) Assignee: International Business Machines Corporation, Armonk, NY (US)

( * ) Notice: Subject to any disclaimer, the term of this patent is extended or adjusted under 35 U.S.C. 154(b) by 182 days.

(21) Appl. No.: 14/960,564

(22) Filed: Dec. 7, 2015

(65) Prior Publication Data

US 2017/0160157 A1  Jun. 8, 2017

(51) Int. Cl.
| | |
|---|---|
| *G01N 7/00* | (2006.01) |
| *G01N 33/00* | (2006.01) |
| *G01L 19/00* | (2006.01) |
| *G01N 1/40* | (2006.01) |

(52) U.S. Cl.
CPC ...... *G01N 33/0014* (2013.01); *G01L 19/0007* (2013.01); *G01N 1/4044* (2013.01); *G01N 33/0063* (2013.01)

(58) Field of Classification Search
CPC ......... G01L 19/0007; G01L 2019/0053; G01L 19/0092; G01L 19/06; G01N 1/2202; G01N 1/2214; G01N 1/4044; G01N 1/405; G01N 33/0013; G01N 33/0014; G01N 33/0036
USPC ............ 73/31.01, 31.02, 31.04, 31.05, 31.07
See application file for complete search history.

(56) References Cited

U.S. PATENT DOCUMENTS 3,567,387 A * 3/1971 Jones ................. G01N 1/00
422/62
5,457,316 A * 10/1995 Cohen ................ G01N 27/622
250/282
5,767,388 A  6/1998 Fleischer et al.
(Continued)

OTHER PUBLICATIONS

Y. Wang et al, "A Review of Carbon Nanotubes-Based Gas Sensors," Journal of Sensors, May 2009, Article ID 24 pages, vol. 2009.
(Continued)

*Primary Examiner* — Benjamin Schmitt
(74) *Attorney, Agent, or Firm* — Vazken Alexanian; Ryan, Mason & Lewis, LLP

(57) ABSTRACT

Systems, devices, and methods are provided for detecting and measuring the concentration of non-reactive gases in a given environment, without having to increase the reactivity of the non-reactive gases through thermal heating. For example, a gas sensor device includes a sensing chamber, a chemical getter element disposed in the sensing chamber, and a pressure sensor device. The sensing chamber is configured to capture a gas sample. The chemical getter element is configured to remove reactive gas species of the gas sample through chemical reaction of the reactive gas species with the chemical getter element at room temperature. The pressure sensor device is configured to measure a pressure of non-reactive gas species of the gas sample, which remains in the sensing chamber after removal of the reactive gas species from the sensing chamber. The pressure measurement is used to determine an amount of the non-reactive gas species present in the sample.

20 Claims, 4 Drawing Sheets

(56) References Cited

U.S. PATENT DOCUMENTS

| | | | | |
|---|---|---|---|---|
| 5,786,529 | A * | 7/1998 | Voss | G01M 3/202 |
| | | | | 73/40.7 |
| 7,308,819 | B2 * | 12/2007 | Kamio | H01J 9/241 |
| | | | | 73/23.2 |
| 2006/0048562 | A1 * | 3/2006 | Oishi | G01N 33/0011 |
| | | | | 73/23.2 |
| 2007/0196256 | A1 * | 8/2007 | Chuntonov | B01D 53/02 |
| | | | | 423/219 |
| 2013/0078113 | A1 * | 3/2013 | Chuntonov | F04B 37/04 |
| | | | | 417/48 |

OTHER PUBLICATIONS

T.A. Miller et al., "Nanostructured Tin Dioxide Materials for Gas Sensor Applications," Functional Nanomaterials, by Kurt E. Geckeler and Edward Rosenberg, 2006, pp. 453-476, Chapter 30.

* cited by examiner

_US 9,910,021 B2_

LOW POWER SENSOR FOR NON-REACTIVE GASES

TECHNICAL FIELD

This disclosure relates generally to gas sensing techniques and, in particular, to systems and methods for sensing non-reactive gases.

BACKGROUND

In general, gas sensors are utilized for various applications in industries such as industrial production (e.g., methane detection in mines), the automotive industry (e.g., detection of polluting gases from vehicles), environmental monitoring, boiler control, etc. Conventional techniques for detecting non-reactive gases such as methane are complex as such techniques are commonly based on selective reaction of the detection gas species. For example, in order to increase the reactivity of a non-reactive gas, a sensor is configured to heat the gas and raise the temperature of the gas to a level that makes it reactive. In particular, commercially available methane sensors use a semiconducting metal oxide film as a sensing element. When the methane gas is heated to a high temperature (e.g., greater than 400 degrees Celsius), the methane molecules dissociate, and the atoms diffuse into the metal oxide film. The work function of the metal oxide film changes due to the presence of adsorbed atoms, and the change in work function is detected by a MOSFET (metal oxide semiconductor field effect transistor) device. Since a high temperature is required to dissociate the methane molecules, the power consumption of such gas sensors (which is required for heating the gas) is in the order of hundreds of mW. This high power consumption is not suitable for portable gas sensors, for example, as the power supply batteries for such portable gas sensors would have be replaced very often.

SUMMARY

Embodiments of the invention include systems, devices, and methods for detecting and measuring the concentration of a non-reactive gas in a given environment, without having to increase the reactivity of the non-reactive gas through thermal heating. For example, in one embodiment of the invention, a gas sensing method includes capturing a gas sample in a sensing chamber, wherein the sensing chamber includes a chemical getter element. The chemical getter element removes the reactive gas species of the gas sample through chemical reaction of the reactive gases with the chemical getter element at room temperature. After removing the reactive gas species from the sensing chamber, a pressure of non-reactive gas species of the gas sample remaining in the sensing chamber is measured. The pressure measurement is used to determine an amount of the non-reactive gas species present in the gas sample.

Another embodiment of the invention includes a gas sensor device. The device includes a sensing chamber, a chemical getter element disposed in the sensing chamber, and a pressure sensor device. The sensing chamber is configured to capture a gas sample. The chemical getter element is configured to remove reactive gas species of the gas sample through chemical reaction of the reactive gas species with the chemical getter element at room temperature. The pressure sensor device is configured to measure a pressure of non-reactive gas species of the gas sample which remains in the sensing chamber after removal of the reactive gas species from the sensing chamber.

In another embodiment of the invention, the gas sensor device is implemented in a gas sensing system, which includes a control system that is configured to control functions of the gas sensor device.

Other embodiments will be described in the following detailed description of embodiments, which is to be read in conjunction with the accompanying figures.

DETAILED DESCRIPTION OF EMBODIMENTS

Embodiments will now be discussed in further detail with regard to systems, devices, and methods for detecting and measuring the concentration of a non-reactive gas in a given environment, without having to increase the reactivity of the non-reactive gas through, e.g., thermal heating. The term "non-reactive gas" as used herein refers to a gas that is highly stable and non-reactive with other elements or compounds at "room temperature." In addition, the term "room temperature" as used herein refers to a temperature in a range of about 0 degrees Fahrenheit to about 100 degrees Fahrenheit, for example. As is known in the art, methane ($CH_4$) is one of the least reactive gases at room temperature. While embodiments of the invention may be described in the context of devices and methods for sensing methane gas, the techniques discussed herein can be implemented with non-reactive gases other than methane.

It is to be understood that various system/device components and methods for detecting non-reactive gases, as generically described and schematically illustrated in the accompanying Figures, may be implemented and designed in a wide variety of different configurations. Thus, the following detailed description of illustrative embodiments, as represented in the Figures, is not intended to limit the scope of the application as claimed, but is merely representative of example embodiments of the invention. Moreover, the same or similar reference numbers are used throughout the drawings to denote the same or similar features, elements, or structures, and thus, a detailed explanation of the same or similar features, elements, or structures will not be repeated for each of the drawings. It is to be understood that the term "about" as used herein with regard to percentages, ranges, etc., is meant to denote being close or approximate to, but not exactly. For example, the term "about" as used herein implies that a small margin of error is present, such as 1-5% or less than the stated amount.

Figure 1:
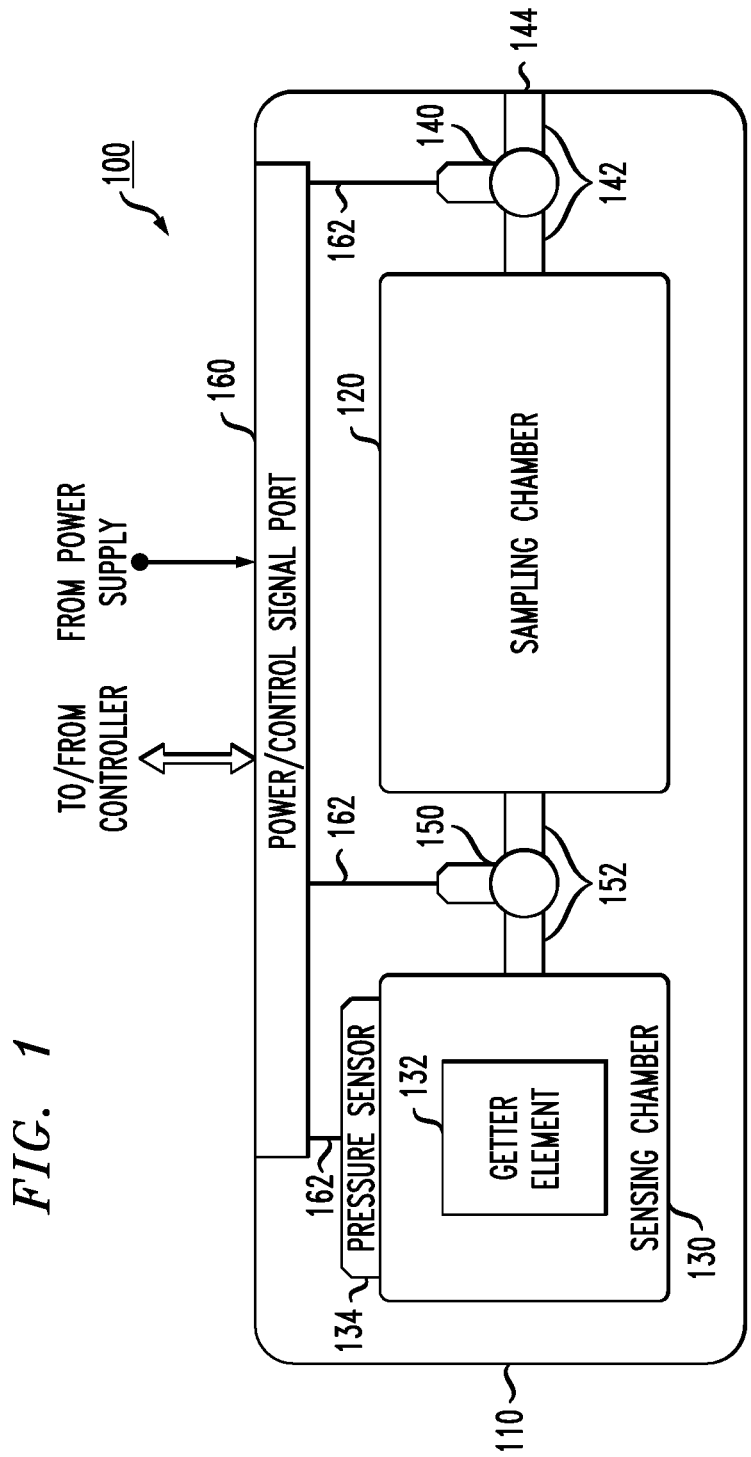
FIG. 1 is a schematic view of a non-reactive gas sensor device according to an embodiment of the invention.

FIG. 1 schematically illustrates a non-reactive gas sensor device according to an embodiment of the invention. In particular, FIG. 1 is a conceptual illustration of a non-reactive gas sensor device 100 comprising a housing 110, a sampling chamber 120, and a sensing chamber 130. The sensing chamber 130 comprises a chemical getter element 132 disposed within the sensing chamber 130, and a pressure sensor 134 disposed within, or operatively connected to, the sensing chamber 130. The gas sensor device 100 further comprises a first gas flow control valve 140, a second gas flow control valve 150, and a power/control signal port 160.

In general, the non-reactive gas sensor device 100 is configured to detect and measure the concentration of a non-reactive gas (e.g., methane) in a given environment at room temperature, without having to heat the non-reactive gas to make it reactive. As explained in further detail below, in one embodiment of the invention, during a gas sensing operation, a gas sample is transferred to the sensing chamber 130 from the sampling chamber 120. The gas sample may comprise a sample of air or some other mixture of gases having a detection gas species depending on the environment being tested. The gas sample may comprise one or more reactive gas species and one or more non-reactive gas species that are being monitored. The reactive gas species of the gas sample is removed through chemical reaction of the reactive gas species with the chemical getter element 132 at room temperature. After removing the reactive gas species from the sensing chamber 130, the pressure of the non-reactive gas species remaining in the sensing chamber 130 is measured using the pressuring sensor 134. The pressure measurement is processed to determine the amount of the non-reactive gas species in the captured gas sample.

In this regard, rather than heating the non-reactive gases (e.g., methane) to make the gases become reactive (as with conventional techniques), embodiments of the invention make use of the non-reactivity of the detection gas species (at room temperature) by utilizing the chemical getter element 132 in the sensing chamber 130 to chemically react with and eliminate all other reactive gases in the gas sample. The partial pressure of the residual gas in the sensing chamber 130 is indicative of the concentration of the non-reactive gas (e.g., methane) in the original gas sample. In this manner, a gas sensing operation is achieved at room temperature with low power consumption, as no heating is necessary and the power consumed by the pressure sensor 134 during the sensing operation is minimal.

The chemical getter element 132 comprises a reactive material that is capable of chemically reacting with all of the reactive gas species which are expected to be present in a sample of gas in a target environment being monitored, but which are not the target detection gas species. For example, in one embodiment of the invention, in a given application where air samples are being monitored for the presence of high levels of methane gas, the chemical getter element 132 comprises a reactive material that is capable of chemically reacting with reactive gas components of air at room temperature. In particular, nearly all of the earth's atmosphere is made up primarily of five reactive gases including nitrogen ($N_2$), oxygen ($O_2$), argon (Ar), carbon dioxide ($CO_2$), and water vapor ($H_2O$), as well as trace amounts of other gases such as neon, helium, hydrogen, methane, etc. In one embodiment of the invention, the chemical getter element 132 comprises a material such as Lithium (Li) which reacts with nitrogen, oxygen, carbon dioxide, and water vapor at room temperature.

In one embodiment of the invention, the chemical getter element 132 may comprise a bulk getter element wherein the reactive material (e.g., Li) of the chemical getter element 132 may comprises a bulk component the reactive material (e.g., blocks, sheets, strips, wires of Li material). In another embodiment, the chemical getter element 132 may comprises a substrate having a coating of the reactive material (e.g., Li) formed on a surface of the substrate. The substrate surface, or coating, may be rough to increase the reactive surface area of the chemical getter element 132.

When the reactive gas molecules of a given gas sample strike the reactive material of the chemical getter element 132, the reactive gas molecules chemically combine with the reactive material of the chemical getter element 132 and are, thus, removed from the sensing chamber 130. For instance, in a given air sample, the reactive gas species of nitrogen ($N_2$), oxygen ($O_2$), carbon dioxide ($CO_2$), water vapor ($H_2O$), and carbon monoxide (CO), chemically combine with the reactive Li material of the chemical getter element 132 to form, e.g., lithium oxide, lithium nitride, etc. In this regard, the reactive materials are adsorbed into, and chemically combined with, the Li material.

On the other hand, the Li material of the chemical getter element 132 is not reactive with other trace gases in the given air sample such as Ar or methane. Although other non-reactive gases such as Ar of the given air sample are not adsorbed by the chemical getter element 132, the expected partial pressure (or concentration) of such non-reactive gases in a normal air sample provides a baseline pressure. If the measured pressure of the residual non-reactive gases remaining in the sensing chamber 130 (after completion of the chemical getting) exceeds the expected baseline pressure, then it is determined that the given air sample includes an abnormal amount of non-reactive gas. For instance, in a given environment where it is anticipated that there can be increased levels of methane in the air, if the measured pressure of the residual non-reactive gases (in the sensing chamber 130) is higher than the expected baseline consisting of Ar (and other small traces of non-reactive gases that commonly exist in air), the difference between the measured pressure and the excepted baseline will indicate the pressure of methane (or some other target detection gas species).

In accordance with embodiments of the invention, the chemical getter element 132 is configured to be replaceable at some point when all of the reactive material (e.g., Li) is consumed after a number of sensing cycles. Indeed, the chemical getter element 132 is configured such that the entire volume of the reactive material (e.g., bulk Li, or Li coating) of the chemical getter element 132 can react with gas (instead of just the exposed surface of the reactive material). In this regard, to predict the lifetime expectancy of the chemical getter element 132, it is desirable to control the volume of air that is exposed to the reactive material of the chemical getter element 132 for each sensing cycle. In one embodiment of the invention, as explained in further detail below, the sampling chamber 120 is implemented to enable fine control over the exact volume of air that is transferred to the sensing chamber 130, and which is exposed to the reactive material (e.g., Li reactant) of the chemical getter element 132 for each gas sensing operation. This allows the useful lifetime of the Li reactant to be predicted with substantial accuracy.

During a sensing operation, the first gas flow control valve 140 is operatively controlled to allow a gas sample (e.g., air sample) in a given environment to flow into the sampling chamber 120 through air piping 142. The air piping 142 comprises an inlet port 144 which is exposed to the given environment. The second gas flow control valve 150 is operatively controlled to allow at least a portion of the gas sample within the sampling chamber 120 to flow into the sensing chamber 130 through air piping 152 in advance of a gas sensing operation. As explained in further detail below, the gas flow control valves 140 and 150 are selectively operated by control signals generated by a control system (e.g., control system 210, FIG. 2) to capture a gas sample (e.g., air) in the sampling chamber 120, and then transfer at least a portion of the air sample to the sensing chamber 130, in which the air sample is isolated and subjected to chemical getting by the chemical getter element 132.

In one embodiment of the invention, the gas flow control valves 140 and 150 comprise electromechanically operated valves, such as solenoid valves, which are controlled by control signals generated by the control system 110. In one embodiment, each of the gas flow control valves 140 and 150 comprises a two-port valve, wherein a given gas flow control valve 140 and 150 is either switched on or switch off to control the flow of air through the air piping 142 and 152.

Moreover, in one embodiment of the invention, the sampling chamber 120 comprises a volume V1 and the sensing chamber 130 comprises a volume V2. The volume V2 of the sensing chamber 130 is selected to have a minimal size/volume that optimizes the sensitivity of the gas sensing operation. Indeed, the volume V2 of the sensing chamber 130 should be small enough so that all the reactive gases in the given gas sample (within the sensing chamber 130) react with the chemical getter element 132 in relatively short amount of time, and without consuming too much volume of the reactive material of the chemical getter element 132. For instance, in one embodiment of the invention, the volume V2 of the sensing chamber 130 is about 1 cubic centimeter or less.

The volume V1 of the sampling chamber 120 can be selected to be the same or greater than the volume V2 of the sensing chamber 130. The relative size of the volumes V1 and V2 will determine how much of the gas sample, which is captured in the sampling chamber 120, will flow into the sensing chamber 130. For example, if the volumes V1 and V2 are the same, then at least half of the volume of the gas sample captured in the sampling chamber 120 will flow into the sensing chamber 130 when equilibrium in pressure is achieved (in this instance, the pressure within the sensing chamber 130 may be below atmosphere pressure, which can be taken into account for the sensing operation). On the other hand, if the volume V1 of the sampling chamber 120 is greater than the volume V2 of the sensing chamber 130, then a greater amount of the captured gas sample will flow into the sensing chamber 130 from the sampling chamber 120. In this regard, the relative volumes V1 and V2 can be selected to control the amount of gas that is transferred from the sampling chamber 120 to the sensing chamber 130.

Furthermore, the amount of reactive material (of the chemical getter element 132) which is consumed per sensing operation, can be determined as a function of the volumes V1 and V2 of the sampling and sensing chambers 120 and 130, as well as the volume V3 and type of the reactive material, as follows. Assume that the chemical getter element 132 comprises a volume V3 of Li reactant, wherein V3=xV2, x<1. For each sensing cycle performed using the chemical getter element 132, the volume of Li reactant that is consumed can be computed as $$6x10^{-14}\left(\frac{V1 V2}{V1+V2}\right).$$

In addition, the total number of useful cycles for the chemical getter element 132 can be computed as $$1700x\left(1+\frac{V2}{V1}\right).$$

In another embodiment of the invention, the sampling chamber 120 is not utilized, and the amount of gas exposure of the chemical getter element 132 can be controlled with a micro-pump to controllably introduce a known volume of gas from the given environment directly into the sensing chamber 130. In another embodiment of the invention, no control mechanism may be implemented to control the amount of gas that is introduced into the sensing chamber 130 for each sensing operation. However, without such control, while the sensing mechanism would still effectively operate, the amount of gas that is introduced into the sensing chamber 130 could vary for each sensing operation, resulting in a variation in the amount of Li reactant that is consumed per sensing cycle. As such, the useful life expectancy of the chemical getter element 132 would not be as predictable.

The pressure sensor 134 can be implemented using one of various types of pressure gauges that are known in the art for gas sensing. The type of pressure sensor that is implemented in the gas sensor device 100 of FIG. 1 can vary depending on the expected range of pressure that will exist in the sensing chamber 130. For example, in one embodiment of the invention, the pressure sensor 134 is implemented using an ion gauge for expected gas pressures in a range of about $10e^{-10}$ torr to about $10e^{-3}$ torr. In another embodiment, the pressure sensor 134 can be implemented using a thermocouple gauge for expected gas pressures in a range of about $10e^{-3}$ torr to about 1 torr (and in some cases 1000 torr). In yet another embodiment of the invention, the pressure sensor 134 can be implemented using a Piranni Gauge, which measures pressure using a using a thermal measurement, for a range of pressures from about 0.1 torr to atmospheric pressure.

The power/control signal port 160 comprises an electrical adaptor or electrical interface that is accessible through the housing 110. The power/control signal port 160 is electrically coupled to a control system 210 or controller (see FIG. 2) to receive control signals that are transmitted to various components of the sensor device 100 such as the pressure sensor 134, and the first and second gas flow control valves 140 and 150 through electrical connections 162 within the sensor housing 110. In addition, pressure sensor measurement signals are transmitted from the pressure sensor 134 to the controller via the electrical connections 162 and power/control signal port 160. Moreover, in one embodiment of the invention, the power/control signal port is connected to a power supply (e.g., batteries) and distributes low power supply voltage to the pressure sensor 134, and the first and second gas flow control valves 140 and 150 through power supply lines of the electrical connections 162 within the sensor housing 110.

Figure 2:
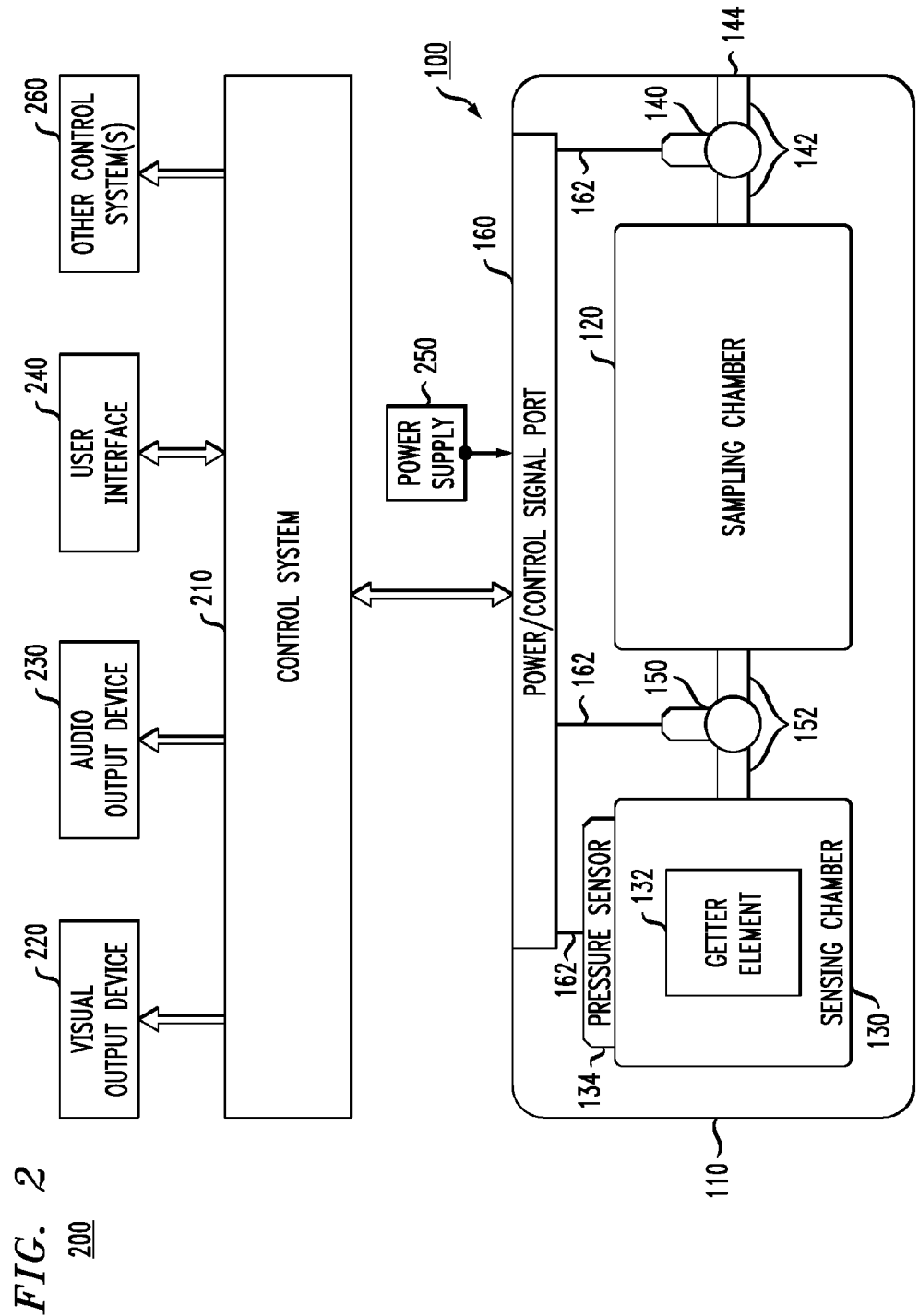
FIG. 2 schematically illustrates a gas sensing system which implements the non-reactive gas sensor device of FIG. 1, according to an embodiment of the invention.

FIG. 2 schematically illustrates a gas sensing system 200 that implements the non-reactive gas sensor 100 of FIG. 1, according to an embodiment of the invention. The gas sensing system 200 comprises a control system 210, a visual output device 220, an audio output device 230, a user interface 240, and a power supply 250. The control system 210 comprises one or more hardware processor elements and memory elements (e.g., ROM, RAM, etc.) to support gas sensing control functions as discussed herein. For instance, as discussed above, the control system 210 is configured to generate control signals to control operation of the gas flow control valves 140 and 150 and the pressure sensor 134. The control system 210 is configured to persistently log pressure sensor measurements that are received from the pressure sensor 134, and process the pressure sensor measurements to determine a concentration of a non-reactive gas (e.g., methane) within a given air sample. In addition, the control system 210 is configured to generate an alarm notification when the concentration of a detection gas species exceeds a pre-specified concentration threshold.

In one embodiment, the control system 210 is configured to generate a visual output notification which is rendered by the visual output device 220. Depending on the system configuration, the visual output device 220 may comprise a computer monitor or a LCD screen of a handheld device, for example, which displays a textual alarm notification. The visual output device 200 may comprise one or more LEDs (light emitting diodes) which display a given color or a given light sequence that is indicative of an alarm condition. In another embodiment, the control system 210 is configured to generate an audible output notification signal that is rendered by the audio output device 230. The audio output device 230 may be implemented using an audio speaker that can process and audio signal to generate an audible alert notification (e.g., alarm ringer), or some other type of output device capable of providing some audible/tactile alarm notification (e.g., vibration or buzzing).

The user interface 240 is configured to allow user access and programmatic control of the gas sensing system 200. For example, the user interface 240 is configured to allow a user to program the control system 210 to automatically perform periodic gas sensing functions (via the gas sensing device 100) according to user-specified control parameters. In addition, the user interface 240 is configured to allow a user to access persistently stored log information regarding previous gas sensing operations and alarm conditions, for example. Moreover, the user interface 240 is configured to allow a user to manually initiate a gas sensing operation on demand by activating a given control button (e.g., a physical or virtually displayed control button).

Depending on the application, the control system 210 can generate one or more control signals that are transmitted to other control systems/devices 260 to control such systems/devices 260 depending on the measured concentration of a detection gas species. For example, in an industrial application (e.g., mining), when a high concentration of methane is detected, the control system 210 can generate a control signal that is configured to shut down some system or process that is causing the increase in methane concentration. In addition, a control signal can be generated to activate an exhaust or filtering system that is configured to reduce/remove the increased level of methane gas in the given environment.

The implementation of the gas sensing system 200 will vary depending on the application. For example, in one embodiment of the invention, the gas sensing system 200 may be implemented as a hand-held device. In this embodiment, the various components 100, 210, 220, 230 and 240 are contained within a housing of the hand-held device. The power supply 250 can be implemented by commercially available replaceable batteries that are suitable for the given application. For a hand-held device implementation, the user interface 240 may be implemented using a combination of physical control buttons that enable the selection of menu items that are displayed on a small LCD screen, for example. In another embodiment, the control system 110 may be implemented as part of a computer system (e.g., FIG. 4) that controls the gas sensing system 210 and other systems in a commercial building, or industrial environment, for example. In this embodiment, one or more gas sensor devices 100 may be strategically disposed in different areas to detect noxious gas, e.g., methane, over a wide area of the given environment.

Figure 3:
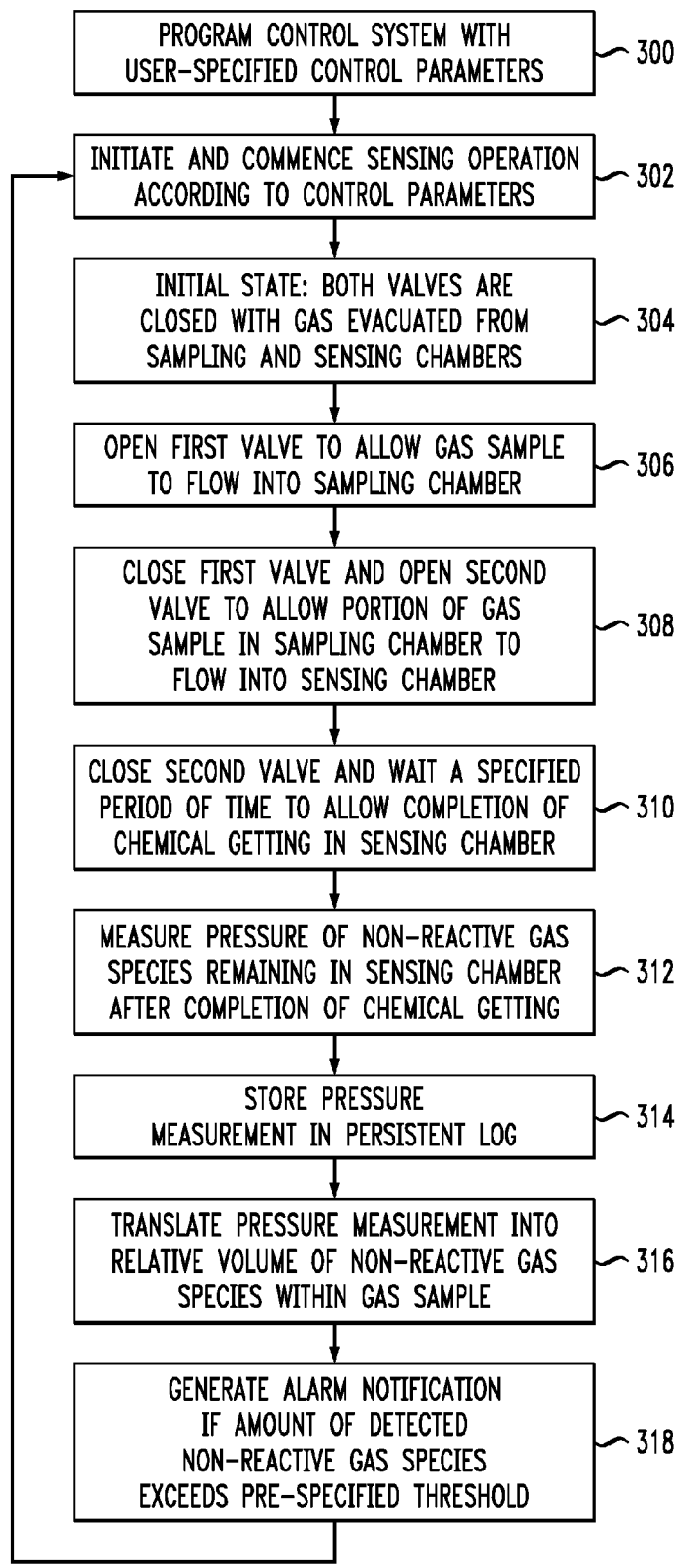
FIG. 3 is a flowchart of a method for detecting and measuring a concentration of non-reactive gas species in a given environment, according to an embodiment of the invention.

FIG. 3 is a flowchart of a method for detecting for the presence of a non-reactive gas in a given environment, according to an embodiment of the invention. In particular, FIG. 3 illustrates a mode of operation of the gas sensing system 200 comprising the non-reactive gas sensor device 100, as shown in FIGS. 1 and 2, according to an embodiment of the invention. For illustrative purposes, the method of FIG. 3 will be discussed in the context of the gas sensing components of FIGS. 1 and 2. Referring to FIG. 3, a user can program the control system 210 of the gas sensing system 200 with various user-specified control parameters that are used to activate and control various system components (block 300). For instance, for automatic gas sensing operations, a user can specify the frequency at which gas sensing operations are performed for a given application (e.g. every minute, every 10 minutes, etc.). Moreover, a user can specify the gas concentration threshold for triggering an alarm condition. In addition, the timing sequence for activating the gas flow control valves 140 and 150, the time period for performing a chemical getting operation before taking a pressure measurement, etc., are parameters that can be specified and optimized for a given application.

Once the gas sensing system 200 is configured, a gas sensing operation will be initiated and commenced according to the user-specified control parameters (block 302). In one embodiment, as noted above, a gas sensing operation can be automatically initiated at a given time based on user-specified parameters. In another embodiment, a gas sensing operation can be manually initiated on demand by a user (e.g., pressing activation button on hand held device), wherein the gas sensing operation is commenced according to other default or user-specified parameters.

In an initial state, both the first and second gas flow control valves 140 and 150 are closed, and any remaining gases from a previous sensing operation are evacuated from the sampling chamber 120 and the sensing chamber 130 (block 304). In one embodiment, a vacuum system (e.g., vacuum pump) is implemented to evacuate any remaining gases in the sampling chamber 120 and the sensing chamber 130, prior to the next gas sensing operation. In one embodiment, a sensing operation can be initiated with a full or partial vacuum in the sampling and sensing chambers 120 and 130. At the very least, any remaining gas in the sampling and/or sensing chambers 120 and 130 should be at some insignificant level that does not adversely affect the sensing accuracy of the next gas sensing operation.

Next, the first gas flow control valve 140 is opened to allow a gas sample (e.g., air sample) from the given environment to flow into the sampling chamber 120 (block 306). The first gas flow control valve 120 is kept open for a minimum period of time (e.g., a fraction of a second) until pressure equilibrium is reached. Once the gas sample is captured in the sampling chamber 120, the first gas flow control valve 140 is closed, and the second gas flow control valve 150 is opened to allow a portion of the gas sample in the sampling chamber 120 to flow into the sensing chamber 130 (block 308). Once pressure equilibrium is reached, between the sampling and sensing chambers 120 and 130, the second gas flow control valve 150 is closed, and the sensing operation waits for a pre-specified period of time to allow completion of a chemical getting of the gas sample in the sensing chamber 130 (block 310).

After the chemical getting is complete and the reactive gas species are removed from the sensing chamber 130, the pressure of the non-reactive gas species of the gas sample remaining in the sensing chamber 130 is measured using the pressure sensor 134 (block 312). The pressure measurement is stored in a persistent log (block 314). For example, as noted above, the pressure measurement is transmitted from the pressure sensor 134 to the control system 210, wherein the pressure measurement is logged and processed by the control system 210. The pressure measurement represents a partial pressure of the non-reactive gas species remaining in the sensing chamber 130 at the completion of the chemical getting operation. The partial pressure is directly proportional to the concentration of the non-reactive gas species in the captured gas sample in the sensing chamber 130.

In this regard, the control system 210 utilizes the pressure measurement to determine the relative volume (e.g., concentration) of the non-reactive gas species contained in the captured gas sample (block 316). If the amount of the detected non-reactive gas species exceeds a pre-specified threshold amount, the control system 210 will generate an alarm notification signal (block 318). As noted above, the alarm notification signal is rendered to output one of an audible alarm, a visual alarm, or a combination thereof.

After the sensing operation is complete, the sensor is placed into an initial state to await a next sensing operation (return to block 302). For example, as noted above, any residual gas in the sampling and sensing chambers 120 and 130 will be released by opening both gas flow valves 140 and 150 and evacuating residual gases in the chamber out from the inlet 144 using a vacuum pump system, for example.

Embodiments of the invention include a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Embodiments of the invention are described herein with reference to flowchart illustrations and/or block diagrams of methods, apparatus (systems), and computer program products. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

These concepts are illustrated with reference to FIG. 4, which shows a computing node 10 comprising a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, handheld or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

Figure 4:
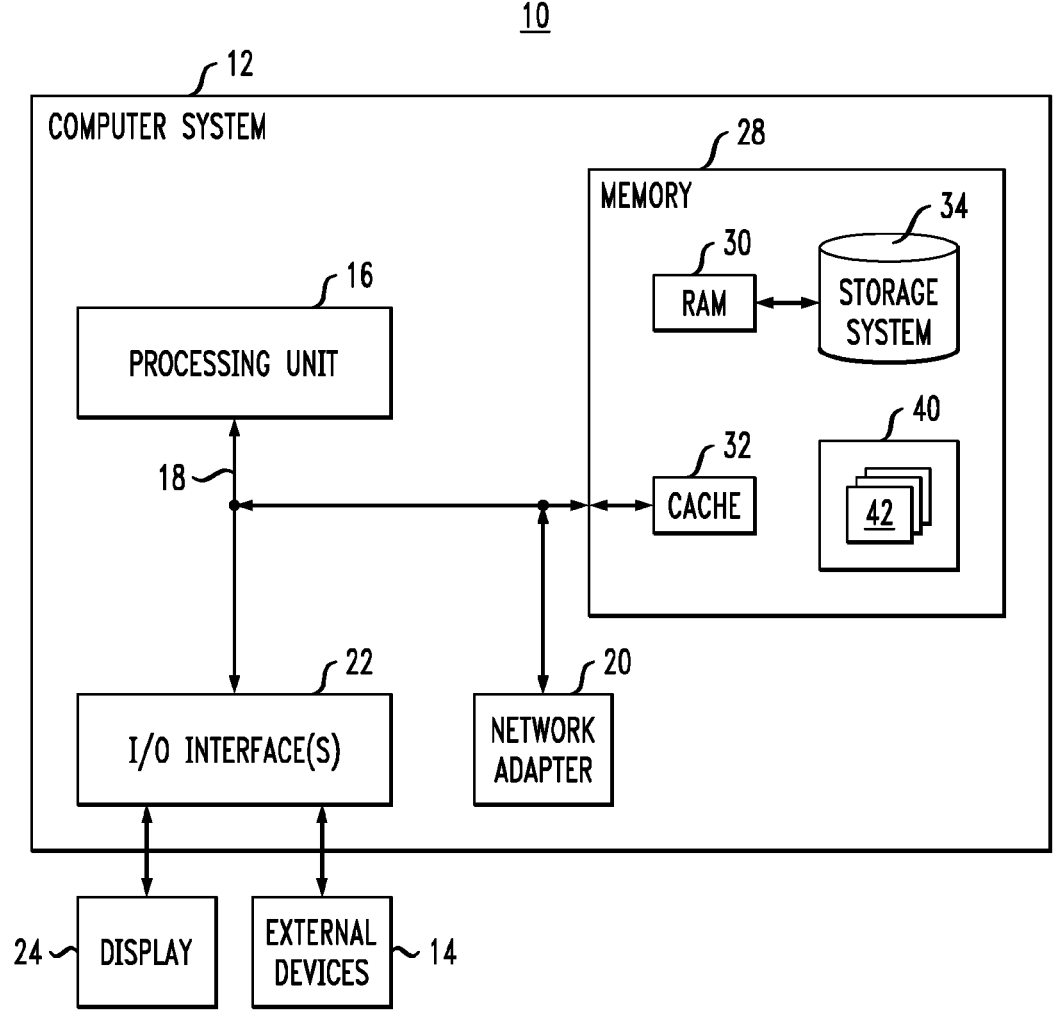
FIG. 4 illustrates a computer system which can be implemented in the gas sensing system of FIG. 2 to controlling a gas sensing device, according to an embodiment of the invention.

In FIG. 4, computer system/server 12 in computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

The bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

The computer system/server 12 typically includes a variety of computer system readable media. Such media may be any available media that is accessible by computer system/server 12, and it includes both volatile and non-volatile media, removable and non-removable media.

The system memory 28 can include computer system readable media in the form of volatile memory, such as random access memory (RAM) 30 and/or cache memory 32. The computer system/server 12 may further include other removable/non-removable, volatile/nonvolatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As depicted and described herein, memory 28 may include at least one program product having a set (e.g., at least one) of program modules that are configured to carry out the functions of embodiments of the invention.

The program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Although exemplary embodiments have been described herein with reference to the accompanying figures, it is to be understood that the invention is not limited to those precise embodiments, and that various other changes and modifications may be made therein by one skilled in the art without departing from the scope of the appended claims.

What is claimed is:
1. A method, comprising:
capturing a gas sample in a sensing chamber of a portable hand-held gas sensor device, the sensing chamber having a chemical getter element disposed therein;
wherein the chemical getter element comprises a reactive material that reacts with the gas sample to remove reactive gas species of the gas sample at room temperature;

after the reactive gas species is removed from the sensing chamber, measuring a pressure of non-reactive gas species of the gas sample remaining in the sensing chamber; and identifying a presence of at least one target non-reactive gas species within the non-reactive gas species based on the measured pressure, wherein the at least one target non-reactive gas species comprises methane.

2. The method of claim 1, wherein the gas sample comprises a sample of air.

3. The method of claim 1, wherein capturing the gas sample in the sensing chamber, comprises:

capturing gas from a given environment in a sampling chamber; and transferring at least a portion of the gas from the sampling chamber to the sensing chamber.

4. The method of claim 1, wherein the reactive gas species comprise nitrogen, oxygen, carbon dioxide, and water vapor.

5. The method of claim 1, wherein the chemical getter element comprises Lithium.

6. The method of claim 1, wherein identifying the at least one target non-reactive gas species comprises comparing the measured pressure to an expected baseline pressure.

7. The method of claim 6, wherein the expected baseline pressure corresponds to an expected pressure of non-reactive gas species in the sensing chamber after the reactive gas species is removed from the sensing chamber.

8. A device, comprising:

a portable hand-held gas sensor device, comprising:

a sensing chamber configured to capture a gas sample;

a chemical getter element disposed in the sensing chamber, wherein the chemical getter element comprises a reactive material that is configured to react with the gas sample to remove reactive gas species of the gas sample at room temperature; and a pressure sensor device configured to measure a pressure of non-reactive gas species of the gas sample, which remains in the sensing chamber after removal of the reactive gas species from the sensing chamber, wherein a presence of at least one target non-reactive gas species within the non-reactive gas species is identified based on the measured pressure, and wherein the at least one target non-reactive gas species comprises methane.

9. The device of claim 8, wherein the gas sample comprises a sample of air.

10. The device of claim 8, further comprising:

a first gas flow control valve;

a sampling chamber; and a second gas flow control valve;

wherein the first gas flow control valve is activated to allow gas from a given environment to flow into the sampling chamber; and wherein the second gas flow control valve is activated to allow at least a portion of the gas in the sampling chamber to flow into the sensing chamber.

11. The device of claim 8, wherein the reactive gas species comprise nitrogen, oxygen, carbon dioxide, and water vapor.

12. The device of claim 11, wherein the reactive material of the chemical getter element comprises a bulk component of the reactive material.

13. The device of claim 11, wherein the reactive material of the chemical getter element comprises a reactive material that is coated on a substrate.

14. The device of claim 8, wherein the chemical getter element comprises Lithium.

15. The device of claim 8, wherein the at least one target non-reactive gas species is identified by comparing the measured pressure to an expected baseline pressure, and wherein the expected baseline pressure corresponds to an expected pressure of non-reactive gas species in the sensing chamber after the reactive gas species is removed from the sensing chamber.

16. A system, comprising:

a portable hand-held gas sensor device, comprising:

a sensing chamber configured to capture a gas sample;

a chemical getter element disposed in the sensing chamber, wherein the chemical getter element comprises a reactive material that is configured to react with the gas sample to remove reactive gas species of the gas sample at room temperature; and a pressure sensor device configured to measure a pressure of non-reactive gas species of the gas sample, which remains in the sensing chamber after removal of the reactive gas species from the sensing chamber;

wherein a presence of at least one target non-reactive gas species within the non-reactive gas species is identified based on the measured pressure, and wherein the at least one target non-reactive gas species comprises methane; and a control system configured to control functions of the gas sensor device.

17. The system of claim 16, wherein the gas sensor device further comprises:

a first gas flow control valve;

a sampling chamber; and a second gas flow control valve;

wherein the first gas flow control valve is activated under control of the control system to allow gas from a given environment to flow into the sampling chamber; and wherein the second gas flow control valve is activated under control of the control system to allow at least a portion of the gas in the sampling chamber to flow into the sensing chamber.

18. The system of claim 16, wherein the reactive gas species comprise nitrogen, oxygen, carbon dioxide, and water vapor at room temperature.

19. The system of claim 16, wherein the chemical getter element comprises Lithium.

20. The system of claim 16, wherein the control system is configured to (i) process the pressure measurement received from the pressure sensor device to determine an amount of the non-reactive gas species present in the gas sample, and (ii) generate an alarm notification if the determined amount of non-reactive gas exceeds a pre-specified threshold.

* * * * *